United States Patent [19]

Lu et al.

[11] Patent Number: 5,571,669

[45] Date of Patent: Nov. 5, 1996

[54] TRANSCRIPTION AND NUCLEIC ACID SEQUENCE DETERMINATION WITH SHORT PRIMER DNA/RNA MOLECULES AND RNA POLYMERASE

[75] Inventors: Ponzy Lu, Bala Cynwyd, Pa.; Fraydoon Rastinejad, New Haven, Conn.

[73] Assignee: The University of Pennsylvania, Philadelphia, Pa.

[21] Appl. No.: 4,383

[22] Filed: Jan. 14, 1993

[51] Int. Cl.$^6$ ............................ C12Q 1/68; C12D 19/34; C07H 21/04; C12N 15/00

[52] U.S. Cl. ............................ 435/6; 435/91.1; 435/91.2; 435/91.3; 435/91.5; 435/91.51; 536/24.33; 536/25.3; 536/25.4; 530/350; 530/820; 935/76; 935/77

[58] Field of Search ............................ 435/6, 91.1, 91.2, 435/91.3, 91.5, 91.51, 1, 2, 3, 8, 16, 17, 76, 77, 183; 536/24.33, 25.3, 25.4; 530/350, 820

[56] References Cited

U.S. PATENT DOCUMENTS

| | | | |
|---|---|---|---|
| 4,683,195 | 7/1987 | Mullis et al. | 435/6 |
| 4,879,214 | 11/1989 | Kornher et al. | 435/91 |
| 5,234,811 | 8/1993 | Beutler et al. | 435/6 |
| 5,266,459 | 11/1993 | Beutler | 435/6 |
| 5,314,813 | 5/1994 | Peterson et al. | 435/172.3 |

OTHER PUBLICATIONS

Konarska et al., *Cell*. vol. 63, 609–618, Nov. 1990.
Konarska et al., Cell, vol. 57, 423–431, May 5, 1989.
*Hawley's Condensed Medical Dictionary*, 11th Ed., Sax and Lewis Eds., Van Nostrand Reinhold Co., New York, 1987, p. 843.
Tabor, *P.N.A.S., U.S.A.*, Feb. 1985, pp. 1074–1078.
Sartoris et alii, *Gene*, 1987, 56 (2–3), pp. 301–7; Abstract Only.
Kandolf et alii, *Proceedings of the National Acvademy of Sciences, U. S. A.*, 82(14), Jul. 1985, pp. 4818–22; Abstract Only.
Gurevich et al., *Anal. Biochem.* 195, pp. 207–213 (1991).
Martin et al., *Biochem*, 27, 3966–3974 (1988).
Chamberlin et al., *The Enzymes* (eds. Boyer, P.D.) New York, Academic Press, vol. XV, pp. 87–108 (1982).
Ogilvie et al., *Proc. Natl. Acad. Sci. USA* 85, pp. 5764–8 (1988).
Milligan et al., *Methods Enzymol.*, vol. 180A, pp. 51–62 (1989).
Axelrod et al., *Biochem*, 24, 5716–5723 (1985).
Geider et al., *Proc. Natl. Acad. Sci. USA* 75, pp. 645–649 (1978).
Uhlenbeck, *Nature* 346, pp. 613–614 (1990).
Tabor et al., *Proc. Natl. Acad. Sci. USA* 84, 4767–4771 (1987).
Tabor et al., *J. Biol. Chem.* 262, 16212 (1987).
Lewis et al., *J. Biol. Chem.* 255, pp. 4928–4936 (1980).
Krupp, *Nucleic Acids Research* 17, 3023–3036 (1989).
Daube & von Hippel, *Science* 258, 1320–1324 (Nov. 20, 1992).

*Primary Examiner*—Stephanie W. Zitomer
*Assistant Examiner*—Bradley L. Sisson
*Attorney, Agent, or Firm*—Seidel, Gonda, Lavorgna & Monaco

[57] ABSTRACT

In vitro transcription of RNA or DNA templates from short RNA or DNA primers is acheived in the absence of a DNA promoter sequence. The progressive nature of the elongation complex according to the present invention allows for increased yields of fully extended transcripts and minimizes aborted RNA chains normally associated with in vitro transcription initiation at a promoter.

24 Claims, 7 Drawing Sheets

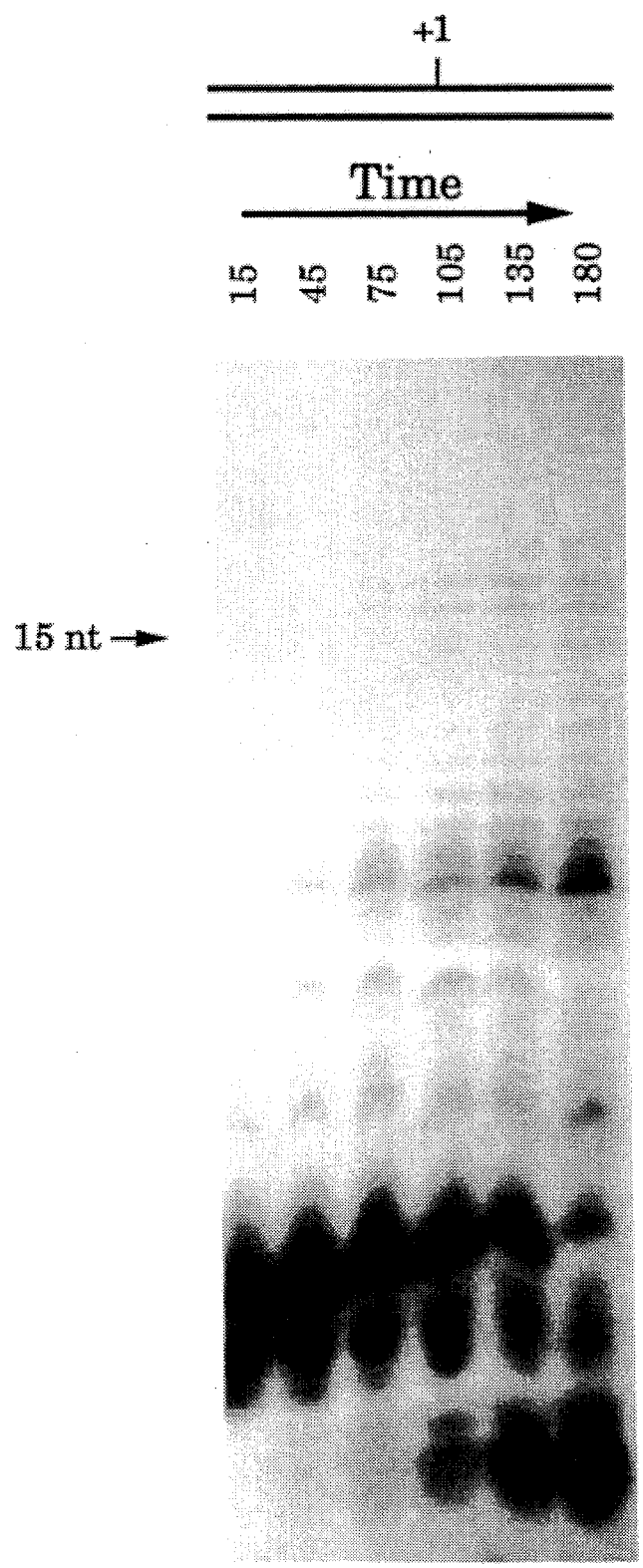
FIG. IA

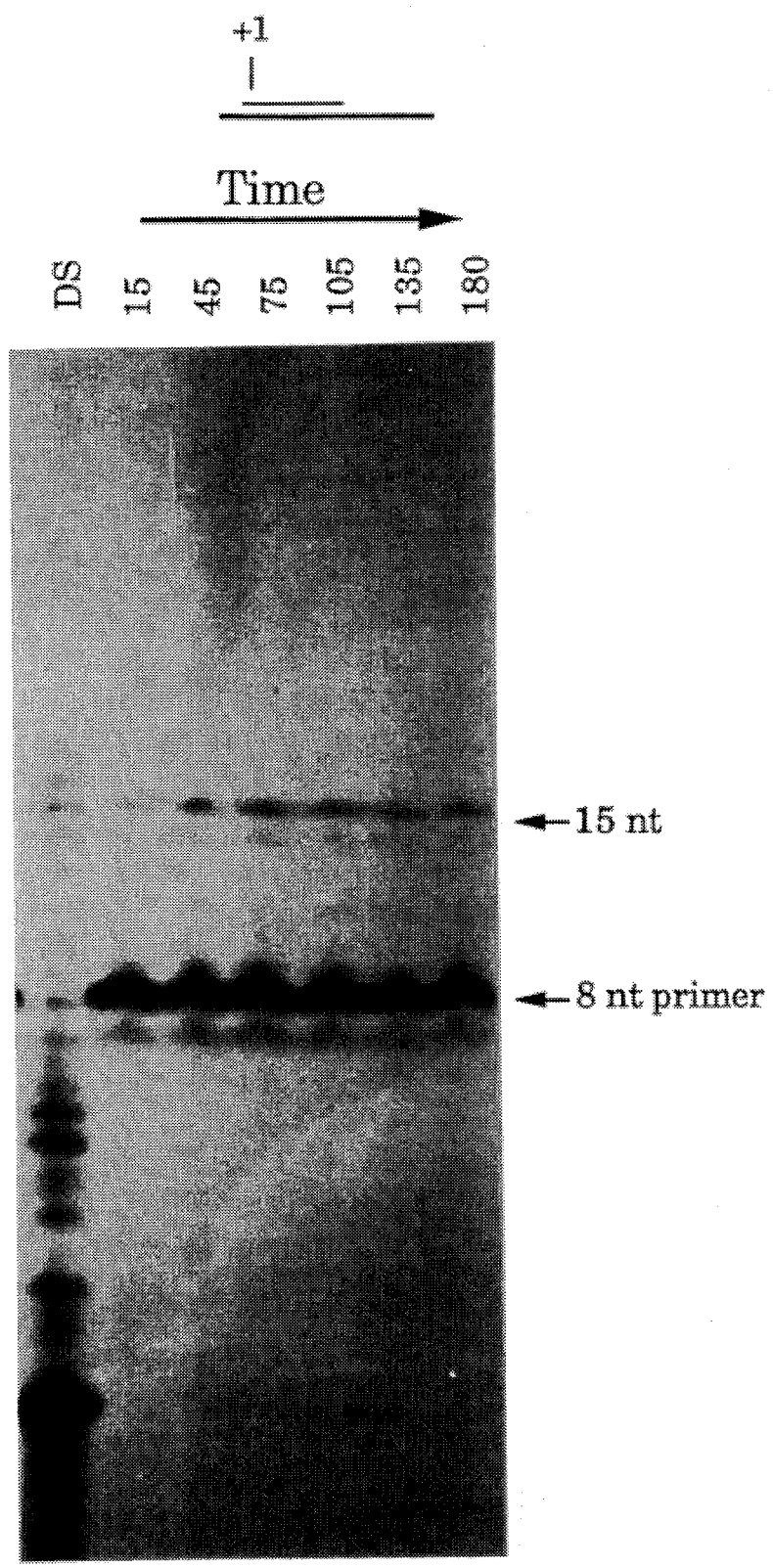
FIG. IC 5,571,669

TRANSCRIPTION AND NUCLEIC ACID SEQUENCE DETERMINATION WITH SHORT PRIMER DNA/RNA MOLECULES AND RNA POLYMERASE

REFERENCE TO GOVERNMENT GRANT

The invention described herein was made in part with government support under grant GM32987 awarded by National Institutes of Health. The government has certain rights in the invention.

FIELD OF THE INVENTION

The present invention relates to the utilization of RNA polymerases which allow extensions of short RNA or DNA primers on longer RNA or DNA single-stranded templates.

BACKGROUND OF THE INVENTION

RNA transcripts of cloned, synthesized, or isolated DNA segments are useful in studying RNA splicing, sequencing DNA segments, and in vitro translation. RNA transcription may be used for RNA sequencing, in producing proteins, and for post-translational modification of proteins. Also, RNA translation may be used to produce more stable biopharmaceuticals such as DNA/RNA chimeras.

In vitro transcription of DNA via RNA polymerases has been used as a step in producing mRNA. The mRNA is in turn used to produce functionally active proteins. Such production of mRNA has been proposed as a means for large scale industrial manufacture of polypeptides. It would provide the milligram or more quantities of mRNA required for large industrial processes.

Bacteriophage RNA polymerases are highly active and preferred for in vitro transcription of DNA. They are composed of a single polypeptide chain, while other RNA polymerases tend to be more complex or have one or more co-factors. The T7, T3, and SP6 RNA polymerases have all been cloned. They are commercially available in large quantities, and can also be readily produced from commerically available vectors.

The RNA polymerase-specific DNA promoter sequences found at the beginning of most genes define the high affinity RNA polymerase binding site from which transcription initiation proceeds. The promoter sequence of a particular RNA polymerase is a DNA segment attached to the template DNA strand upstream from the portion to-be-transcribed into RNA (i,e., at the 5'-end of the template). The promoter allows the RNA polymerase to attach to the DNA template sequence near the site to-be-transcribed, so that transcription may be initiated.

It is generally regarded that each species of RNA polymerase is specific for a particular promoter sequence. Each of the three bacteriophage RNA polymerases (T7, T3, and SP6) has its own specific DNA promoter sequence.

After the RNA polymerase has attached to the promoter sequence of the template and transcription has been initiated, the promoter sequence releases the RNA polymerase. The RNA polymerase then continues transcription along the template until (1) it runs out of RNA starting materials, (2) the transcription reaction is terminated by a particular nucleotide, nucleoside or analog, (3) transcription is spontaneously aborted when the RNA polymerase and the template prematurely disassociate, or (4) the end of the DNA template is reached.

Most DNA-dependant RNA polymerases have been shown to accept RNA as a template for polymerization of NTPs. Such polymerization has been characterized as usually being inefficient and nonspecific for both transcription initiation and termination. The DNA-dependant polymerase of T7 will accurately and efficiently replicate a short RNA template under some circumstances. See, Konarska et al., *Cell* Vol. 57, 423–431 (1989). The short single-stranded RNA template does not have appropriate promoter sequences. Rather, it has a specific binding site to which the T7 RNA polymerase attaches and begins transcription. This was discovered by Konarska et al after high levels of unanticipated RNA side-products (called X-RNA or Y-RNA) were generated without any explanation. Other unexplained side products observed were head-to-tail RNA polymers and complementary double-stranded RNA of the X-RNA or Y-RNA.

Additional experiments by Konarska et al., *Cell* Vol. 63, 609–618 (1990) showed that the X-RNA or Y-RNA served as a template for itself. The origin of X-RNA or Y-RNA was unclear. The only sources for the X-RNA and Y-RNA have been some preparations of T7 RNA polymerase. Contamination of the preparations with X-RNA, Y-RNA, or a precursor was stated as the likely reason for the RNA side products.

Obtaining RNA products from these X- or Y-RNA templates was puzzling since the templates did not have the DNA promoter sequence specific for the attachment of the T7 RNA polymerase. Konarska et al. also conducted experiments showing that other RNA polymerases did not produce RNA products from X- or Y- RNA templates unless a promoter was attached.

The Konarska et al. products contained palindromic sequences (tandem inverted repeats), which are known to be recognition sites for some RNA polymerases. Thus, certain segments along these RNA templates (possibly a palindromic sequence) were able to specifically bind the T7RNA polymerase tightly enough to permit transcription of the RNA template to begin. None of the naturally occurring RNAs tested (including total RNA from *E. coli* or Hela cells and tRNA from *E. coli*, yeast, or Hela tRNA) served as an efficient template for transcription by T7 RNA polymerase. Moreover, it was noted that when these other RNAs were present, replication of X-RNA was strongly inhibited.

Thus, Konarska et al. state that replication of the X-RNA or Y-RNA was specific to T7 RNA polymerase. The very closely related T3 RNA polymerase (80% homology with T7 RNA polymerase) was unable to replicate the X-RNA or Y-RNA without a promoter sequence.

Lewis et al. (J. Biol. Chem., 255, No. 10, 4928–4936 (1980)) showed that wheat germ RNA polymerase II will transcribe one of the nicked strands of a double-stranded Simian Virus 40 DNA to produce a complementary RNA strand without a DNA promoter. Wheat germ RNA polymerase II has a large, complex structure, which is similar in structure and sensitivity to mammalian RNA polymerase II. One of the two DNA strands must be nicked to provide a 3'-hydroxy end for transcription to begin, since no transcription was observed with intact DNA. Lewis et al. reported that DNA transcription with RNA polymerases is neither specific or very controllable. A DNA strand must be nicked to start transcription, which ends when the RNA polymerase encounters another nick in the double-stranded DNA.

Moreover, Lewis et al. reported that transcription of deproteinized DNA by wheat germ polymerase II in vitro was doubtful. Specifically, a DNA-binding protein co-factor was thought necessary to effect biologically relevant transcription. Apparently, the binding protein co-factor serves as a bridge which binds the RNA polymerase and the DNA template until translation of the template is progressing. Thus, the binding cofactor protein replaces the binding provided by a promoter sequence specific for the RNA polymerase.

Production of RNA by wheat germ RNA polymerase from nicked double-stranded DNA proceeds slowly. As transcription occurs, the double strands of DNA must be melted (made to unwind) to provide a single DNA template strand for translation. Some of the products are hybrid DNA/RNA strand (chimeras) and some of the products are entirely RNA, but there is apparently limited control over which products will be obtained. The nicking process is unpredictable as to the location of nicks along an uncharacterized DNA sequence, and the subsequent RNA products are also unpredictable.

E. coli RNA polymerase, in the presence of its binding co-factor protein (DNA binding protein I), can transcribe a DNA template to produce a RNA chain. (See, Geider et al., Proc. Natl. Acad. Sci., U.S.A., 75, No. 2, 645–649 (1978)). No nicking is required, and there is apparently limited control over which products will be obtained. The transcription is random as to the initiation location along a DNA sequence, and the subsequent RNA products are also unpredictable. (See also, Lewis et al., cited above).

The bacteriophage T7 RNA polymerase, as is typical for other RNA polymerases, is very specific for its particular promoter sequence. It is a single sub-unit polypeptide that can transcribe genes in vitro from highly conserved T7 promoter sequences in the absence of other proteins (Chamberlain et al., *The Enzymes*, Boyer, ed. New York Acad. Press, 3rd ed., p. 85 (1982); Dunn et al., *M. Mol. Biol.* 166, 477–535 (1983)). The efficiency and high promoter specificity of T7 RNA polymerase has made it useful for in vitro generation of small mRNA (Geider, *Proc. Natl. Acad, Sci. USA* 75, 645–649 (1978)) as well as for cloning and in vivo gene expression (Guruvich et al., *Analytical Biochem* 195, 207–213 (1991); Lewis et al., *J. Biol. Chem.* 255, 4928–4936 (1980); Milligan et al., *Methods Enzymol.* Vol. 180a, ed., 50–52 (1989)). Because of its simplicity and minimal requirements T7 RNA polymerase has been practical for studying the complex mechanisms involved in transcription.

However, there is a significant difficulty encountered with the use of T7 RNA polymerase for generating RNA transcripts. Large quantities of contaminating short RNA molecules in the range of 2–8 NTPs are generated, which comprise incomplete RNA translation products. These short chains are believed to be due to premature release of the RNA polymerase by the promoter sequence. The RNA polymerase apparently discontinues translating the template after its release by the promoter.

As a result of the large numbers of abortive initiation side products, the yield of the desired transcript from T7 mediated transcription is low. The abortive side products typically result in a yield which is an order of magnitude lower than the yield expected from the NTP reagents consumed. This has required use of terminator NTPs as marking units, and separation of short RNA molecule contaminants from marked terminated sequences as part of RNA sequencing procedures.

Further, when double stranded DNA is used as the template for T7 transcription, the RNA polymerase must melt an eight base pair DNA segment. This allows for base pair complementarity between the eight base pair segment and the template strand. The melting must continue as the double strand is unwound and transcribed.

Accordingly, there is a need for efficiently generating RNA transcripts without producing large amounts of short RNA molecules as contaminating side-reaction products. Particularly, there is a need to efficiently produce long chain RNA transcripts. Also, there is a need for a method to transcribe a DNA template or RNA template without requiring either an RNA polymerase-specific DNA promoter sequence or an RNA polymerase-specific binding co-factor protein. Further, there is a need for a method of transcribing a DNA template, which is not part of two substantially complementary strands that have been nicked to provide RNA transcription initiation and termination sites.

SUMMARY OF THE INVENTION

The present invention provides a method for transcribing a DNA target segment, and thereby producing an RNA segment substantially complementary to said DNA target segment, comprising:

(a) providing a DNA template segment containing the DNA target segment, (b) hybridizing to said DNA target segment a complementary RNA primer comprising about 7 or more nucleotides to produce a modified template comprising a double-stranded hybrid DNA/RNA segment, and (c) exposing said modified template to an RNA polymerase which transcribes said DNA target segment by extension of said RNA primer.

In a second embodiment, the present invention provides a method for transcribing an RNA target segment, and thereby producing a DNA/RNA chimera segment, wherein the RNA portion of said DNA/RNA chimera segment is substantially complementary to said RNA target segment, comprising:

(a) providing an RNA template segment containing the RNA target segment, (b) hybridizing to said RNA target segment a complementary DNA primer comprising about 7 or more nucleotides to produce a modified template comprising a double-stranded hybrid DNA/RNA segment, and (c) exposing said modified template to an RNA polymerase which transcribes said RNA target segment by extension of said DNA primer.

In a third embodiment, the present invention provides a method of sequencing an RNA target segment comprising:

(a) providing a DNA primer segment comprising about 7 or more nucleotides, wherein said DNA primer segment is complementary to a portion of said RNA target segment, (b) hybridizing said DNA primer segment to said RNA target segment to provide a modified RNA segment, and (c) exposing said modified RNA segment to an RNA polymerase which transcribes said modified RNA target segment by extension of said DNA primer to produce a DNA/RNA chimera segment hybridized to said modified RNA segment, (d) separating said DNA/RNA chimera segment from said RNA target segment strand by melting the double strands, and (e) determining the nucleotide sequence of said chimera segment obtained in step (d) to provide the nucleotide sequence of said RNA target segment.

In an alternative method of sequencing an RNA target segment, steps (a)–(d) as set forth in the third embodiment above are followed by:

(e') reverse transcribing said chimera segment obtained in step (d) to produce a cDNA segment hybridized with said chimera segment, (f) separating said cDNA segment from said DNA/RNA chimera segment, and (g) determining the nucleotide sequence of said cDNA segment to provide the nucleotide sequence of said RNA target segment.

In a fourth embodiment, the present invention provides a method of sequencing a DNA target segment comprising:

(a) providing an RNA primer segment comprising about 7 or more nucleotides, wherein said RNA primer segment is complementary to a portion of said DNA target segment, (b) hybridizing said RNA primer segment to said DNA target segment to provide a modified DNA segment, (c) exposing said modified DNA segment to an RNA polymerase which transcribes said DNA target segment by extension of said RNA primer to produce an RNA segment hybridized to said modified DNA segment, (d) separating said RNA segment from said DNA target segment, and (e) analyzing said RNA segment obtained in step (d) to determine the sequence of said DNA target segment.

In an alternative method of sequencing a DNA target segment, steps (a)–(d) as set forth in the fourth embodiment above are followed by:

(e') reverse transcribing said RNA segment obtained in step (d) to produce a cDNA segment hybridized to said RNA segment, (f) separating said cDNA segment from said RNA segment, and (g) determining the nucleotide sequence of said cDNA segment to provide the nucleotide sequence of said DNA target segment.

In a fifth embodiment the present invention provides a method for producing an oligo- or polynucleotide segment comprising a RNA segment which incorporates one or more nucleoside triphosphate analogs by transcribing a DNA target segment to produce an RNA segment substantially complementary to a portion of said DNA target segment, which method comprises:

(a) providing a DNA template segment containing the DNA target segment, (b) hybridizing to said DNA template segment a complementary RNA primer comprising about 7 or more nucleotides to produce a modified template having a double-stranded hybrid DNA/RNA segment, and (c) exposing said modified template to an RNA polymerase which transcribes said DNA target segment by extension of said RNA primer to produce an RNA segment, wherein during the transcription step one or more native nucleoside triphosphate reactants is/are replaced or supplemented by one or more nucleoside triphosphate analog reactants whereby the resulting RNA segment incorporates said nucleoside triphosphate analog.

In a sixth embodiment the present invention provides a method for producing an oligo- or polynucleotide segment comprising a DNA/RNA chimera segment having an RNA segment which incorporates one or more nucleoside triphosphate analogs by transcribing an RNA target segment and producing a DNA/RNA chimera segment wherein the RNA portion of said DNA/RNA chimera segment is substantially complementary to said RNA target segment, the method comprising:

(a) providing an RNA template segment containing the RNA target segment, (b) hybridizing to said RNA template segment a complementary DNA primer comprising about 7 or more nucleotides to produce a modified template comprising a double-stranded hybrid DNA/RNA segment, and (c) exposing said modified template to an RNA polymerase which transcribes said RNA target segment by extension of said DNA primer to produce a DNA/RNA chimera segment, wherein during the transcription step one or more native nucleoside triphosphate reactants is/are replaced or supplemented by one or more nucleoside triphosphate analog reactants whereby the resulting DNA/RNA chimera segment incorporates said nucleoside triphosphate analog.

In a seventh embodiment the present invention provides a kit for transcribing an RNA segment comprising (a)
  (i) a DNA primer segment comprising at least about 7 deoxynucleotides, which segment is complementary to a portion of said RNA segment to be transcribed, or
  (ii) deoxynucleotide triphosphates for providing said DNA primer segment complementary to said RNA segment to be transcribed, (b) an RNA polymerase, and (c) a magnesium buffer solution.

In an eighth embodiment, the present invention provides a method for producing an RNA/cDNA chimera segment, which comprises (a) providing a DNA template segment containing a DNA target segment, (b) hybridizing to said DNA template segment a complementary RNA primer comprising about 7 or more nucleotides to produce a modified template comprising a double-stranded hybrid DNA/RNA segment, and (c) exposing said modified template to an RNA polymerase which transcribes said DNA target segment by extension of said RNA primer to produce an RNA template, (d) separating said RNA template from said DNA target segment, (e) providing a second RNA primer which is complementary to a portion of said RNA segment obtained in step (d), (f) hybridizing said second RNA primer with said RNA template to provide an RNA duplex of said RNA primer and RNA template, (g) exposing said RNA duplex to a reverse transcriptase, which reverse transcribes said RNA segment by extending said RNA primer to produce an RNA/cDNA chimera segment hybridized to said RNA template, (h) separating said RNA/cDNA chimera from said RNA template.

Particularly preferred embodiments of the present invention as described above utilize RNA polymerases, which are stable during storage, comprise a single polypeptide chain, and do not require a specific polymerase-binding co-factor for transcription activity. Even more preferred are RNA polymerases selected from the group consisting of T7 RNA polymerase, T3 RNA polymerase, SP6 RNA polymerase, and the like.

To more fully describe the present invention definitions of the following terms are provided. These definitions apply to any use of the terms in the above text, in the following text, and in the claims.

"Hybrid" refers to a double-stranded complex of complementary base pairs, wherein one strand comprising an RNA segment is hybridized to a strand comprising a complementary DNA segment.

"Chimera" refers to a strand of nucleotides, which in a linear relationship comprises at least one DNA segment and at least one RNA segment.

"Chimera hybrid duplex" refers to a double-stranded complex of complementary base pairs wherein one strand comprises a DNA/RNA chimera segment hybridized with another strand, which other strand comprises a DNA strand or an RNA strand.

"Target" segment refers to a segment on a DNA or RNA template strand, which segment is to-be-transcribed.

"Reverse transcription" means the transcription of RNA into complementary DNA.

"Native nucleoside triphosphate" or "native nucleotide" means any one of the naturally occurring normal precursors of RNA, i.e., ATP, GTP, CTP, or UTP.

"Nucleoside triphosphate analog" or "nucleotide analog" means any nucleoside triphosphate analogous to a native nucleotide, but which contains one or more chemical modifications over the native nucleotide.

The duration of the reactions (minutes) is shown above the lanes. The NTPs starting materials were labeled with $\gamma^{32}P$. Thus, the figure shows $\gamma^{32}P$-labeled molecules on a radiograph; the location for the 15-mer fully extended molecule type is indicated by an arrow.

Figure 1B:
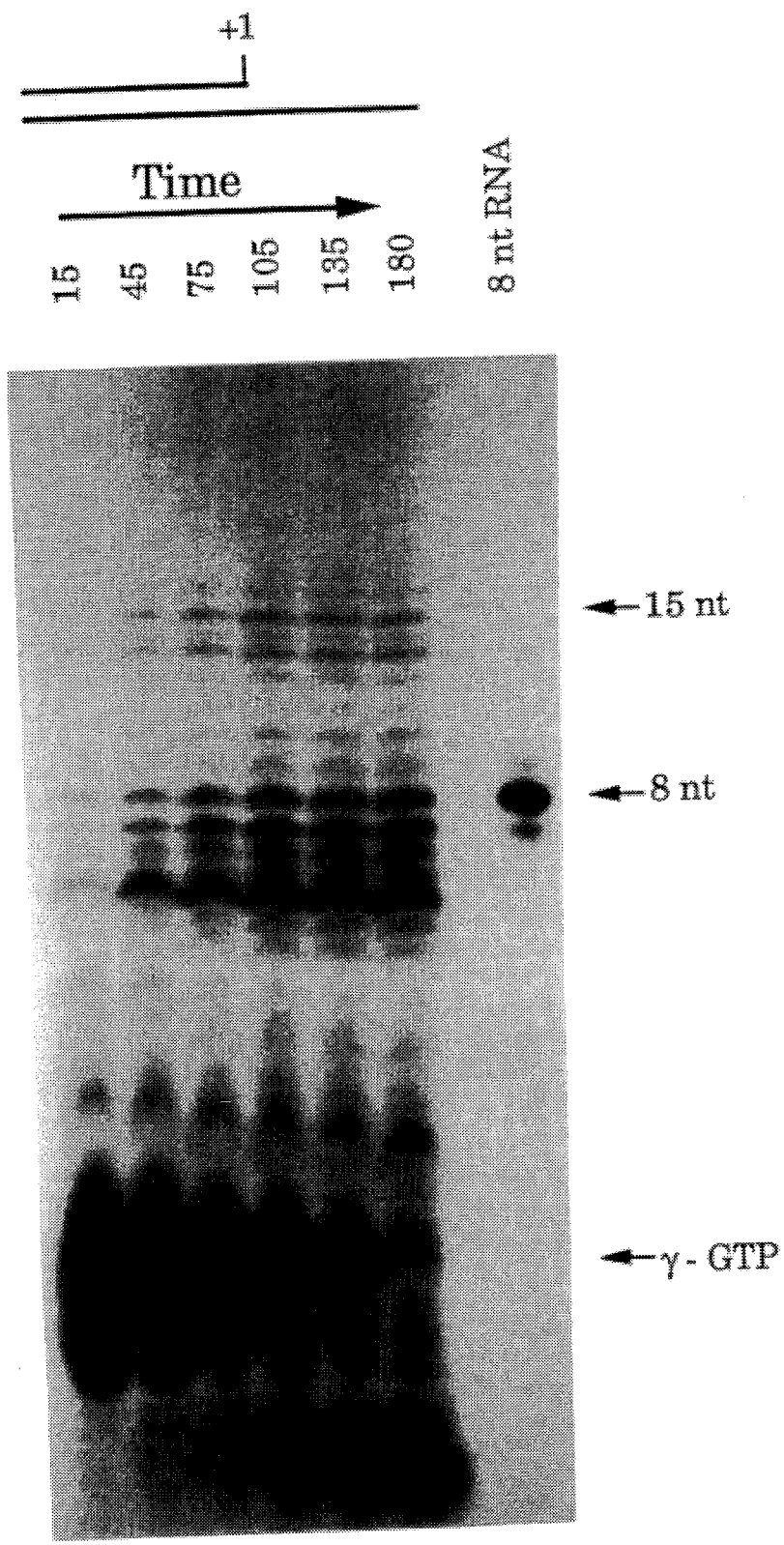
FIG. 1A shows the T7 RNA polymerase runoff transcription of a 15 nucleotide RNA from a double-stranded promoter/double-stranded template DNA molecule. Each strand of the double-stranded 15 nucleotide template is joined to one of the promoter strands. This structure is schematically illustrated above the time-line in the figure. The +1 point indicates where the promoter ends and the template begins. The double strands are melted and transcription initiated at the +1 point. Transcription continues to the right of the +1 point, but only one of the template strands is transcribed. The sequence for each of the double strands is indicated in Table 2 (at 1a) and in the sequence listing as SEQ ID NOs 1 and 3.

FIG. 1B shows T7 RNA polymerase runoff transcription of a 15 nucleotide RNA from a double-stranded promoter/single-stranded template DNA molecule. One of the two strands is 14 nucleotides longer than the other since only the promoter portion and one nucleotide of the longer strand is hybridized with its complement. This structure is schematically illustrated above the time-line in the figure. The +1 point indicates where the promoter ends and the template begins. The sequences for the two strands are shown in Table 2 (at 1b) and schematically drawn above the lanes. The duration of the reactions (minutes) is shown above the lanes. The NTPs starting materials were labeled with $\gamma^{32}P$. Thus, the figure shows $\gamma^{32}P$-labeled 15-mer, 8-mer, and GTP molecules on a radiograph; the location for each of the molecule types is indicated by an arrow. The lane marked 8 nucleotides RNA contains the $\gamma^{32}P$-labeled SEQ ID NO:5 corresponding to the first 8 nucleotides of the runoff (see Table 2).

FIG. 1c shows T7 RNA polymerase runoff transcription of a 15 nucleotide RNA from a promoterless single-stranded template DNA molecule hybridized with a labeled eight nucleotide RNA primer. The sequences of the hybridized template and primer are shown in Table 2 (at 1c) and as SEQ ID NOs: 4 and 5 in the sequence listing. The structure of the hybridized strands is shown schematically above the lanes. The +1 point indicates the first nucleotide of the 8 nucleotide RNA primer, which primer is to be extended to the right from its eighth position. The duration of the reactions (minutes) is shown above the lanes. The NTPs starting materials were labeled with $\gamma^{32}P$. Thus, the figure shows $\gamma^{32}P$-labeled 15-mer extended primer molecules and the 8-mer primer molecules on a radiograph; the location for each of the molecule types is indicated by an arrow.

Figure 2:
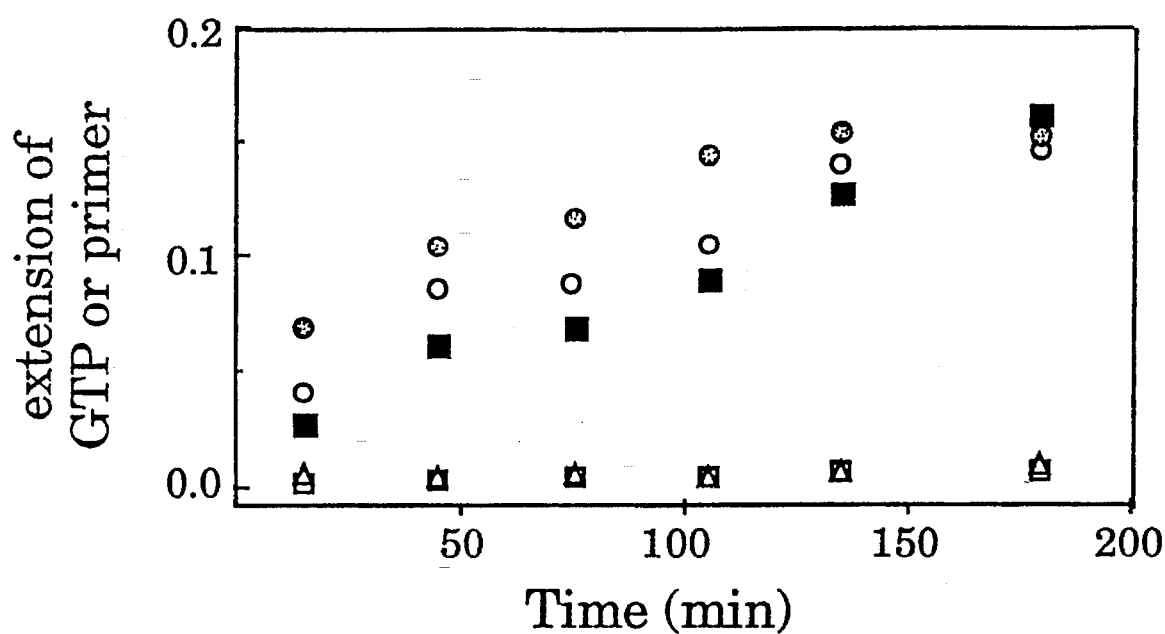

FIG. 2 shows the full length and aborted extensions of an initiating molecule ($\gamma^{32}P$-labeled GTP or RNA) in T7 RNA polymerase transcription reactions as functions of time. The y-axis indicates the fraction of the initiating molecule extended into RNA. The open squares and open triangles are the fractions $\gamma^{32}P$-labeled GTP extended into 15-mer runoff RNA from the reactions shown in FIGS. 1a and 1b, respectively. The filled squares are the fractions of $\gamma^{32}P$-labeled 8-mer RNA primer extended into the 15-mer RNA shown in FIG. 1c. The open and shaded circles are the fractions of $\gamma^{32}P$-labeled GTP extended into the aborted RNA chains in the range of two to eight nucleotides from FIGS. 1a and 1b, respectively.

Figure 3A:
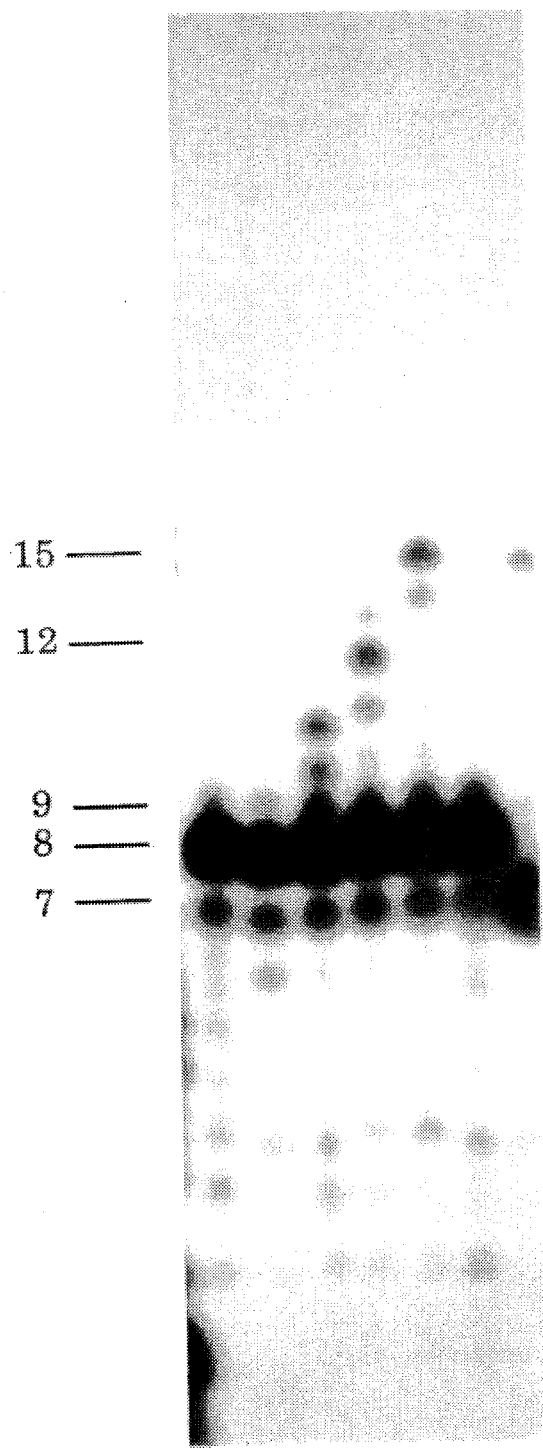

FIG. 3a (lanes 1–7) shows step-wise RNA transcription by T7 RNA polymerase of one of the strands on a double-stranded promoter/double-stranded template DNA molecules as compared to extension of a $\gamma^{32}P$-labeled RNA primer on a promoterless single-stranded template DNA molecule hybridized with said $\gamma^{32}P$-labeled eight-nucleotide RNA primer. The templates in the reaction of lanes 1–7 are the templates shown in Table 2, at (1a) and (1c), respectively. All the reactions contained T7 RNA polymerase and an 8-nucleotide (lanes 1–6) or 7-nucleotide (lane 7) primer that contained the only $\gamma^{32}P$-labeled species of the reaction. The 7-nucleotide primer lacked the 3'-terminal nucleotide of the 8-nucleotide primer shown in Table 2 at (1c) or (2c). The reaction loaded in lane 2 did not contain NTPs; lane 3 contained UTP; lane 4 contained UTP + GTP; lanes 1, 5, and 7 contained UTP + GTP + CTP; and lane 6 contained GTP + CTP + ATP. The locations of the initiating primers and those of the correct elongation products (based on the template sequences in Table 2 and the limited NTPs added) are shown to the left of the lanes. The RNA sizes formed in the presence of limed NTP substrates are predominantly those expected from the template sequences. However n-1 products (and to a lesser extent n+1 products) were also produced.

Figure 3B:
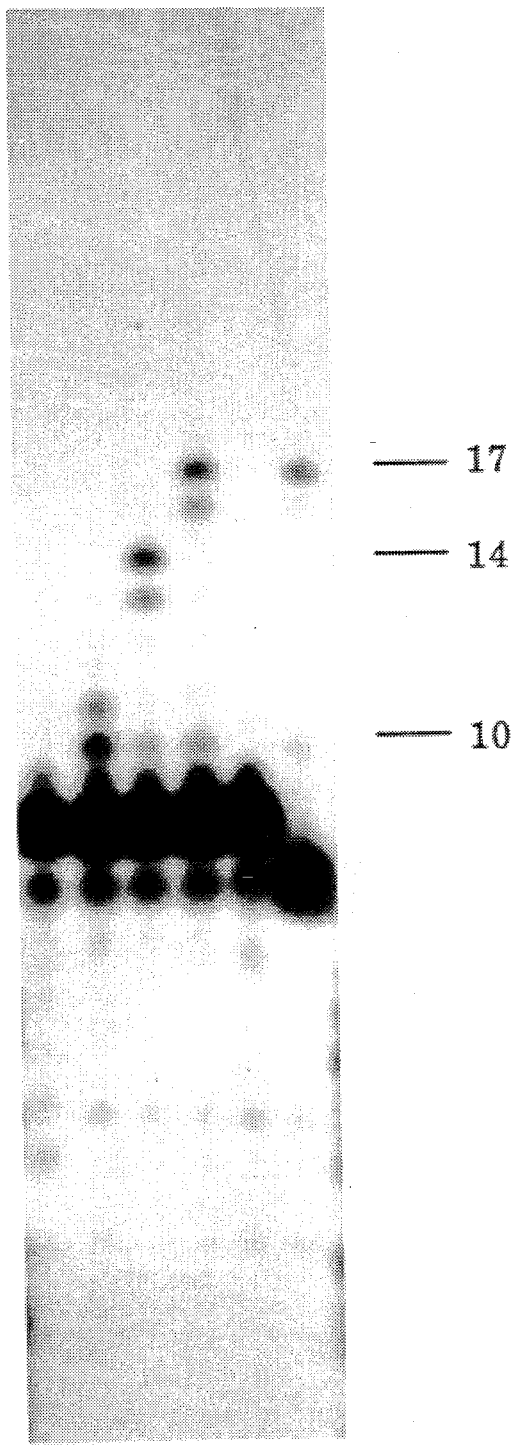

FIG. 3b (lanes 8–13) shows step-wise RNA transcription by T7 RNA polymerase of one of the strands on a double-stranded promoter/double-stranded template DNA molecules as compared to extension of a $\gamma^{32}P$-labeled RNA primer on a promoterless single-stranded template DNA molecule hybridized with said $\gamma^{32}P$-labeled eight-nucleotide RNA primer. The templates in the reaction of lanes 8 and 9–13 were the templates shown in Table 2, at (2a) and (2c), respectively. All the reactions contained T7 RNA polymerase and an 8-nucleotide (lanes 8–12) or 7-nucleotide (lane 13) primer that contained the only $\gamma^{32}P$-labeled species of the reaction. The 7-nucleotide primer lacked the 3'-terminal nucleotide of the 8-nucleotide primer shown in Table 2 at (1c) or (2c). The reaction loaded in lane 9 contained UTP; lane 10 contained UTP + GTP; lanes 8, 11 and 13 contained UTP + GTP + CTP; and lane 12 contained GTP + CTP + ATP. The locations of the initiating primers and the correct elongation products (based on the template sequences in the table and the limited NTPs added) are shown to the right of the lanes. The RNA sizes formed in the presence of limed NTP substrates are predominantly those expected from the template sequences. However n–1 products (and to a lesser extent n+1 products) were also produced.

Figure 4A:
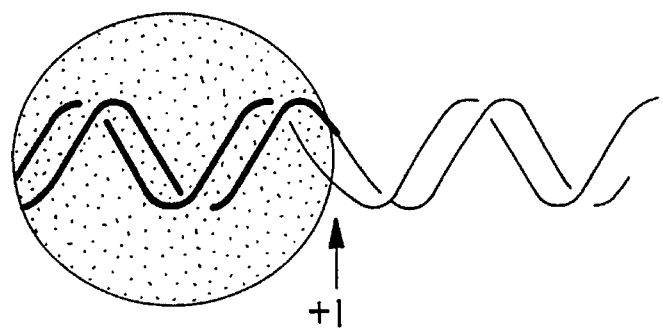

FIG. 4a is a diagram of a double-stranded promoter (bold lines)/double-stranded template (light lines) DNA molecule, wherein the double-stranded promoter is attached to an RNA polymerase (shaded area). A conventional in vitro transcription is shown being initiated at the +1 area. Transcription of one of the template strands to produce an RNA segment is preceded by RNA polymerase melting about 7 or 8 base pairs of the double-stranded template adjacent to the double-stranded promoter.

Figure 4B:
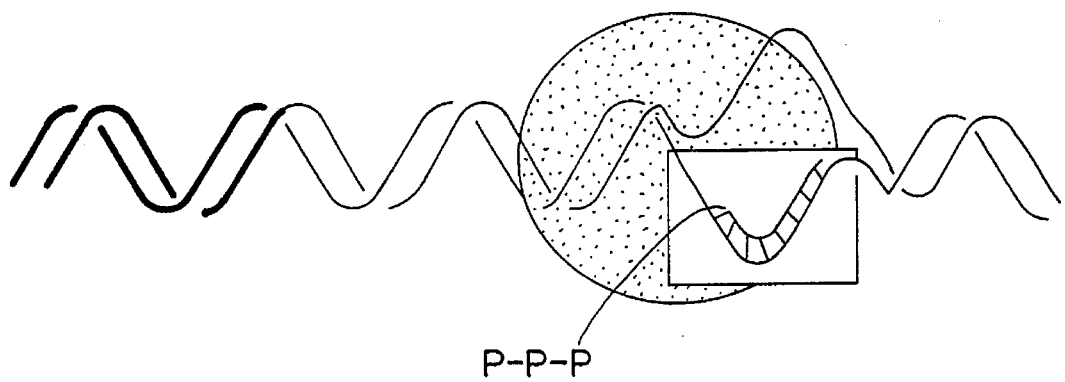

FIG. 4b is a diagram of a RNA polymerase transcription of a double-stranded promoter (bold lines)/double-stranded template (light lines) DNA molecule in the elongation phase. Shown is a trailing triphosphate terminated RNA segment having about 7 or 8 nucleotides at the 3'-end of the RNA segment base hybridized to 7 or 8 of the nucleotides on one of the strands of the DNA template. The hybridized segment is at the point where the template double strands are melted and a RNA polymerase is attached. The 7 or 8 base pairs forming a hybrid DNA/RNA double strand (see area in box) are attached to an RNA polymerase (shaded area). Conventional in vitro transcription of the elongation complex extends the 3'-end of the RNA segment along the DNA template. The template double-strands are melted by the RNA polymerase as the RNA segment is extended.

Figure 4C:
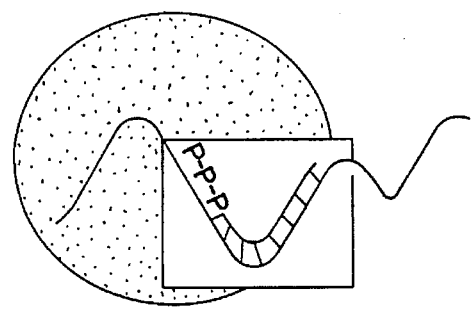

FIG. 4c is a diagram of a DNA/RNA complex having a DNA promoterless single-stranded template DNA molecule hybridized with a triphosphate-terminated eight-nucleotide RNA primer, wherein the complex is attached to an RNA polymerase (shaded area). The 7 or 8 base pairs forming a hybrid DNA/RNA double strand (see area in box) by nascent RNA base-pairing with the template strand are attached to an RNA polymerase (shaded area). Seven or eight nucleotides of RNA base-pairing with the template strand is sufficient to form active complexes capable of RNA polymerase primed RNA synthesis. In vitro transcription according to the present invention initiates at the hybrid DNA/RNA double strand area in the box and extends the 3'-end of the RNA primer along the DNA template.

DETAILED DESCRIPTION OF THE INVENTION

The present invention is based upon a surprising, newly discovered property for RNA polymerases, such as T7 RNA polymerase, T3 RNA polymerase, SP6RNA polymerase, and the like. Applicants have discovered that RNA polymerases will extend RNA or DNA primers on long RNA or DNA single target strand templates. Surprisingly, primer extension proceeds in the absence of a promoter DNA sequence specific for the polymerase. Moreover, primer extension does not require a polymerase-specific binding sequence, or a polymerase-specific co-factor.

A common difficulty encountered with the use of T7 RNA polymerase for generating RNA transcripts is the large quantities of short RNA molecules in the range of 2–8 nucleotides aborted prior to the establishment of processivity (>8 nucleotides) and full length RNA synthesis (Martin et al., Biochem. 27, 3966–3974 (1988)) (see FIG. 1a). Because these aborted RNA chains also form when the non-template strand is absent (FIG. 1b), their formation is unrelated to displacement of that strand in the open complex (Martin et al., id., (1988). The limited interaction between nascent RNA chains <8 nucleotides and the template-enzyme complex may lead to failed elongation if these starting ternary complexes have a rate of dissociation that is comparable to or exceeds that of further elongation. A substantial fraction of the NTP substrates are consumed in the production of aborted products.

The initiation of RNA synthesis and clearance of the promoter-template region beyond about +7 to +8, therefore, seem to be the dominant barriers to processivity, causing the aborted RNAs to be produced approximately tenfold molar more efficiently than the desired transcript (FIG. 2).

The invention provides a method of RNA chain extension in vitro where an about 7-nucleotide RNA strand (and preferably about 8-nucleotide RNA strand) is annealed with and extended along a single strand of template DNA (FIG. 1c). The octanucleotide region of RNA-DNA duplex is sufficient for efficient T7 RNA polymerase binding and can completely replace the T7 promoter function in initiating transcription. The RNA transcript extended from the hybrid is produced without the usual accumulation of aborted chains (FIG. 1c) and the mole fraction of initiating molecule extended to full length is ten to twenty fold increased (FIG. 2, Table 2).

Transcription from double stranded promoter-template DNA can not be efficiently initiated with an RNA primer even if it is complementary to the first eight nucleotides of the template strand (FIGS. 3a and 3b, lanes 1,8). Primer extension into the full length RNA transcript depends on the ability of the RNA polymerase to unwind an eight base-pair DNA segment to allow base pairing with the template strand.

Single-stranded template DNA molecules overcome the strand displacement requirement and facilitate complementary RNA synthesis. Transcription then proceeds from the eight nucleotide primer RNA with addition of the required substrate nucleotide triphosphates (NTPs) in the usual 5' to 3' direction and terminates at the end of the template (FIGS. 3a and 3b, lanes 3–5 and 9–11). The NTP requirements are strictly governed by the complementary template strand sequence (lanes 6,12). Seven nucleotide RNA primers are also extended (lanes 7,13).

DNA at the 5' and 3' ends of the complementarity site do not have specific sequence requirements, nor length requirements. Templates containing zero to seventeen nucleotides upstream of the RNA primer binding sites have been successfully used with no apparent effect on primer RNA extension. Thus, the polymerase binding at the primer binding sites is not mediated by a preferred enzyme binding at the double stranded blunt end of the duplex. Furthermore, the identity of the first NTP covalently linked to the 3' end of the RNA primer can be varied, since both a seven-nucleotide primer ending in adenosine and eight-nucleotide primer ending in uridine were able to form covalent links with the first substrate UTP (FIGS. 3a and 3b).

Since in the method according to the present invention chain elongation proceeds from the first unpaired DNA base 3' to the primer binding site, any region of a single-stranded DNA molecule can be potentially transcribed. An RNA primer is simply designed which has the appropriate RNA primer-DNA complementarity to the target region to-be-transcribed. RNA synthesis by primer extension overcomes the necessity of starting with GTP required at the +1 site of T7 promoters (Milligan et al., *Nucl. Acids Res.* 15, 8783–8798, 1987).

The promoter DNA sequences found at the beginning of most genes define the RNA polymerase entry site from which transcription initiates with a nucleoside triphosphate and proceeds along the template DNA. The present invention provides an alternative scheme of in vitro transcription with T7RNA polymerase where the promoter sequence is not required. The enzyme can form an active transcriptional complex at the 3' end of a short RNA molecule hybridized to a longer single strand of DNA.

The short RNA molecule hybridized to the longer DNA strand defines the start location of transcription on the DNA and is incorporated as the primer. The DNA strand sequence serves as the template for chain elongation.

The primer extension system according to the present invention mimics a ternary elongation complex. That complex is the required intermediate structure in gene transcription where the enzyme has entered and cleared the promoter. Transcription can be completely uncoupled from promoter requirements. The processive nature of this elongation complex allows increased yields of fully extended transcripts and minimizes aborted RNA chains normally associated with in vitro initiation at a promoter.

With primer RNA concentrations of 120 µM, the RNA elongation yields are comparable or somewhat increased over yields obtained with promoter-directed transcription. Ten to twenty fold more primer RNA is extended into full length transcripts (using primer extension in the absence of promoter) than when initiating GTP is extended from the +1 site of promoters.

Accordingly, RNA transcript yields are amplified without increasing substrate NTP concentrations.

However, since the primer is the limiting reagent and is converted irreversibly to product, increasing its initial concentration or providing sustained additions in repeated transcription cycles results in substantial improvements in RNA yields.

Primer-sized RNA molecules are available from total chemical synthesis methods (Ogilivie et al., *Proc. Natl. Acad. Sci., U.S.A.*, 85, 5764-57-68 (1988); Wu et al., *Nucl. Acids. Res.*, 17, 3501–3517 (1989)). However, longer molecules in the size range of messenger RNAs can not be easily synthesized due to exponential increase of failures. However, with the technique according to the present invention, primer-sized, synthetic RNA molecules are used to produce improved yields of high molecular weight RNA species. Such species are useful for genetic and biophysical studies (Uhlenbeck, *Nature* 346, 613–614, (1990)).

The absence of promoter from the template DNA sequence is likely to further prevent abortive fall off transcripts associated with promoter clearance. The absence of promoter allows the enzyme to bind preferably at the primer-template complex. Usually, enzyme concentrations necessary for the present non-promoter primer extension method must exceed those in standard promoter employing methods (1–5 µM) as RNA polymerases usually bind the primer-templates with lower affinity than it binds the promoter.

RNA chains extended beyond eight nucleotides are preferred since they are less subject to abortive termination. The RNA polymerase enzyme is processive after clearing the +1 to +8 region adjacent to the promoter. As a result, the transcription method described according to the present invention allows the bulk of the used NTP substrates to be incorporated in the full length transcript and substantially lower amounts are lost on aborted RNA chains.

The primer-template-polymerase complex according to the present invention, which is employed to initiate transcription, resembles the elongation ternary complex at a point in the gene away from the promoter where the non-template strand is displaced and the template strand is base-paired with a region of the nascent mRNA (FIG. 4). Thus the present invention characterizes RNA extension in a complex of RNA polymerase, template strand, and nascent RNA, and experimentally identifies the minimal components that direct processive transcription elongation.

The present invention advantageously uses a primer segment comprising more than about 7-nucleotide triphosphates (NTPs) or deoxynucleotide triphosphates (dNTPs). The primer segment is complementary to a target segment of a template strand and will hybridize to the target segment on the template strand. Preferably, the primer segment is an RNA segment if the target segment is a DNA segment. The primer segment is preferrably a DNA segment if the target segment is an RNA segment.

The template segment comprising the target segment can be either a synthetic or naturally occurring polynucleotide segment. It can be synthesized or obtained by techniques well known in the art. (See for example, Sambrook et al., *Molecular Cloning*, 2nd ed., Cold Spring Harbor Laboratory Press, pp 1.21–1.52, 2.60–2.80, 6.22–6.34, and 7.6–7.23 (1989)).

Hybridization conditions and reagents referred to or used throughout the description of the present invention and claims are well known in the art. (See for example, Sambrook et al., *Molecular Cloning*, 2nd ed., Cold Spring Harbor Laboratory Press, pp 7.52–7.56, 7.74–7.78, and B.1–B.16 (1989)).

Transcription conditions and reagents referred to or used throughout the description of the present invention and claims are well known in the art.

Examples of typical conditions and reagents for RNA polymerase transcription are readily found in the literature. (See for example, Chamberlain et al., *The Enzymes*, Boyer, ed. New York Acad. Press, 3rd ed., p. 85 (1982); Dunn et al., *M. Mol. Biol.* 166, 477–535 (1983)); Geider, *Proc. Natl. Acad. Sci. USA* 75, 645–649 (1978)); Guruvich et al., *Analytical Biochem* 195, 207–213 (1991); Lewis et al., *J. Biol. Chem.* 255, 4928–4936 (1980); Martin et al., *Biochem.* 27, 3966–3974 (1988); and Milligan et al., *Methods Enzymol.* Vol. 180a, ed., 50–52 (1989)).

All of the above documents generally refer to DNA promoter initiated, or palindromic sequence initiated, transcription. The ideal concentration of the RNA polymerase for promoter initiated, or palindromic sequence initiated transcription is somewhat lower than the ideal polymerase concentration required for the present invention. Typically, transcription initiation by promoter or palindrome requires an RNA polymerase concentration of about 1 µM to about 5 µM of the RNA polymerase. The RNA polymerase concentration according to the present process is about an order of magnitude higher. Preferably, RNA polymerase concentration is from about 5 µM to about 150 µM, more preferably from about 10 µM to about 80 µM, and most preferably, from about 35 µM to about 55 µM.

The transcription procedures according to the present invention may also utilize conventional reverse transcription to produce either cDNA or RNA/cDNA chimeras. Enzymes, reagents, reaction conditions and reagent concentrations required for reverse transcription are well- known in the art and will not be described here. (See for example, Sambrook et al., *Molecular Cloning*, 2nd ed., Cold Spring Harbor Laboratory Press, pp 5.52, 5.58, 7.79–7.83, and B.1–B.16 (1989)).

Some procedures according to the present invention result in double-stranded nucleotide segments. A separation step is included to separate the complementary strands by melting the duplex and isolating at least one of the single strands. Such separation procedures are well known in the art. Duplex denaturing conditions include, for example, low salt concentrations and elevated temperatures, or a combination of both.

Once hybrid double-strands are melted to form two single strands, a strand comprising an RNA segment (RNA strand or DNA/RNA chimera strand) can be readily separated from the mating DNA segment strand. Procedures for separating DNA and RNA are well-known in the art. Alternatively, if the desired product is a cDNA, the RNA strand or segment can be digested using an RNase and the cDNA then purified using procedures well known in the art. Examples of separation procedures are sucrose gradient density separations, poly(A) or other polynucleotide tagged column removal, and gel electrophoresis techniques. Electrophoresis of radioactive labeled RNA to obtain and isolate an RNA segment is preferred. Advantageously, NTP analogs having unusual electrical properties may be added as a substrate during transcription to enhance separation.

Nucleic acid sequencing procedures such as those summarized in Watson et al., *Recombinant DNA*, 2nd ed., pages 63–69, are well-known in the art. (See, Holly, Sci. Am., 214(2), 30–39 (1966); Fiers et al., Nature, 260, 500–507 and 810 (1976); Sanger et al., F. Mol. Biol. 13, 373–398 (1965); Sanger et al., F. Mol. Biol. 94, 444–448 (1977); Sanger et al., F. Mol. Biol. 265, 678–695 (1977); Sanger et al., Proc. Natl. Acad. Sci., U.S.A., 74, 5463–5467 (1977); Fiers et al., Nature, 273, 113–120 (1976); Reddy et al., Science, 200, 494–502 (1978); and Sutcliffe, Cold Spring Harbor Symp. Quant. Biol., 43, 77–90 (1979). The conditions and reagents are also well-known. See also the Sanger RNA sequencing procedure as described in Sambrook et al., Molecular Cloning, 2nd ed., Cold Spring Harbor Laboratory Press, pp 7.37, 13.3–13.14, and C.13 (1989)). Procedures for DNA sequencing analysis are also well-known (e.g., the Maxam-Gilbert Sequencing, Maxam et al., Proc. Natl. Acad. Sci. U.S.A., 74:560 (1977); *Sambrook et al., Molecular Cloning*, 2nd ed., Cold Spring Harbor Laboratory Press, pp 13.78–13.95 (1989)).

Examples of synthetic and modified NTP analogs and chain terminating 3' ddNTPs useful in the practice of the invention are set forth in Table 1, below. Other examples are well-known in the art (See for example, Sambrook et al., Molecular Cloning, 2nd ed., Cold Spring Harbor Laboratory Press, pp C.1–C.13 (1989); and Axelrod et al, Biochem. 24, p. 5716–5723 (1985).

TABLE 1

| Table III: Modified nucleoside triphosphates as substrates for T7 RNA polymerase | | |
|---|---|---|
| | Incorpation into RNA | Reference |
| ATP analog | | |
| 8-Br-ATP | + | Milligan |
| [α-S]ATP (Sp)* | + | Griffiths |
| [α-S]ATP (Rp)* | − | Griffiths |
| 3'-O-methyl-ATP | + (terminates) | Axelrod |
| 3'-dATP | + (terminates) | Axelrod |

TABLE 1-continued

| Table III: Modified nucleoside triphosphates as substrates for T7 RNA polymerase | | |
|---|---|---|
| | Incorpation into RNA | Reference |
| GTP analog | | |
| 7-Me-GTP | − | Milligan |
| ITP (+ priming dinucleotide) | + | Axelrod |
| ITP (− priming dinucleotide) | − | Axelrod |
| 3'-dGTP | + (terminates) | Axelrod |
| CTP analog | | |
| 3'-dCTP | + (terminates) | Axelrod |
| UTP analog | | |
| 5-FUTP† | + | Milligan |
| 5-BrUTP | + | Milligan |
| 4-Thio-UTP | + | Milligan |
| 6-Aza-UTP | + | Milligan |
| Pseudo-UTP | + | Milligan |
| 5-hexamethyleneamino-UTP | + | Milligan |
| 3'-dUTP | + (terminates) | Axelrod |

*Sp and Rp refer to the diasteroisomers of ATP αS
†FUTP incorporation into RNA transcripts is further documented in this work using fluorine NMR and gel electrophoresis.

The complete citations for the three articles listed as references in Table 1, above, are: Milligan, Nucleic Acids Res. 15, 8783–8798 (1987); Giffiths, Nucleic Acids Res. 15, 4145 (1987); and Axelrod, Biochemistry 24, 5716 (1985).

The Examples given below are provided to more specifically describe the invention and are merely descriptive of the invention which is not limited to them.

In Example 1, provided are T7 RNA polymerase runoff transcription of a 15 nucleotide RNA from a double-stranded promoter/double-stranded template DNA molecule and T7 RNA polymerase runoff transcription of a 15 nucleotide RNA from a double-stranded promoter/single-stranded template DNA molecule. The starting materials and results for Example 1 are set forth in Table 2, below, and are illustrated by FIGS. 1a and 1b.

In Example 2, provided are the T7 RNA polymerase runoff transcription of promoterless DNA templates and a labeled RNA primer. The starting materials and results for Example 2 are set forth in Table 2, below, and are illustrated by FIGS. 1c and 3.

In Example 3, provided are provides the T7 RNa polymerase runoff transcription of promoterless DNA templates with a labeled RNA primer. It compares an 8-mer primer to a 7-mer primer regarding the rate of transcription to provide full length RNAs. The number of smaller RNAs (less than full length RNAs) was determined to compare transcription efficiency and primer size.

EXAMPLE 1

Double-Stranded Promoter-Initatiated RNA polymerase Transcription of a Single Strand on Double-Stranded and Single-Stranded DNA Templates The double-stranded and single-stranted DNA template reactants are schematically represented by FIGS. 4a and 4b, respectively. The actual sequences of the templates are listed in Table 2. All reactions were carried out at room temperature in 70 mM HEPES buffer pH 7.85, 5 mM $MgCl_2$, 1.5 mM nucleoside triphosphate (NTP) substrates (shown in Table 2) and 4000 units/ml RNasin (Promega). T7 RNA polymerase concentrations were 5 µM, DNA concentration was 1 µM, and the label was $\gamma^{32}$P-GTP (2% v/v of 2mCi/ml 10Ci/mmol). All transcription reactions were initiated by enzyme addition and terminated by adding equal volume of 8M urea. BME (0.7M final), tRNA (0.2 mg/ml final) and EDTA (0.4 mM final) were then added. The nucleotides were extracted after chloroform/isoamyl addition, and ethanol precipitated prior to denaturing gel electrophoresis. The results are shown in FIGS. 1a and 1b (promoter directed transcription reactions).

To determine the fraction of the initiating molecules (γ-labeled GTP) incorporated into full length transcripts, the bands corresponding to runoff RNA transcripts were excised from the gels and their radioactive counts determined and divided by the total counts of the transcription reaction. The fractional incorporation of γ-labeled GTP into aborted products 2–8 nucleotides (nts) long was likewise determined.

FIG. 1a shows T7 RNA polymerase runoff transcription of a 15 nucleotide RNA from a double-stranded promoter/single-stranded template DNA molecule. One of the two strands is 14 nucleotides longer than the other since only the promoter portion and one nucleotide of the longer strand is hybridized with its complement. This structure is schematically illustrated above the time-line in the figure. The +1 point indicates where the promoter ends and the template begins. The sequences for the two strands are shown in Table 2 (at 1b) and schematically drawn above the lanes. The duration of the reactions (minutes) is shown above the lanes. The NTPs starting materials were labeled with $\gamma^{32}$P. Thus, the figure shows $\gamma^{32}$P-labeled 15-mer molecules on a radiograph; the location for each of the molecule types is indicated by an arrow. The lane marked 8 nucleotides RNA contains the $\gamma^{32}$P-labeled SEQ ID NO:5 corresponding to the first 8 nucleotides of the runoff (see Table 2).

FIG. 1b shows T7 RNA polymerase runoff transcription of a 15 nucleotide RNA from a promoterless single-stranded template DNA molecule hybridized with a labeled eight nucleotide RNA primer. The sequences of the hybridized template and primer are shown in Table 2 (at 1c) and as SEQ ID NOs: 4 and 5 in the sequence listing. The structure of the hybridized strands is shown schematically above the lanes. The +1 point indicates the first nucleotide of the 8 nucleotide RNA primer, which primer is to be extended to the right from its eighth position. The duration of the reactions (minutes) is shown above the lanes. The NTPs starting materials were labeled with $\gamma^{32}$P. Thus, the figure shows $\gamma^{32}$P-labeled 15-mer extended primer molecules, the 8-mer primer molecules and GTP molecules on a radiograph; the location for each of the molecule types is indicated by an arrow.

FIG. 2 shows the full length and aborted extensions of an initiating molecule ($\gamma^{32}$P-labeled GTP or RNA) in T7 RNA polymerase transcription reactions as functions of time. The y-axis indicates the fraction of the initiating molecule extended into RNA. The open squares and open triangles are the fractions $\gamma^{32}$P-labeled GTP extended into 15-mer runoff RNA from the reactions shown in FIGS. 1a and 1b, respectively. The filled squares are the fractions of $\gamma^{32}$P-labeled 8-mer RNA primer extended into the 15-mer RNA shown in FIG. 1c. The open and shaded circles are the fractions of $\gamma^{32}$P-labeled GTP extended into the aborted RNA chains in the range of two to eight nucleotides from FIGS. 1a and 1b, respectively.

EXAMPLE 2

RNA Primer-Initiated Promoterless RNA Polymerase Transcription of a Single-Stranded DNA template All reactions were carried out at room temperature in 70 mM HEPES buffer pH 7.85, 5 mM MgCl$_2$, 1.5 mM nucleoside triphosphate (NTP) substrates (shown in Table 2) and 4000 units/ml RNasin (Promega). The enzyme concentration of RNas117 for each of the reaction was 120 µM, and the primer RNA sequences were labeled at their 5' phosphates. The results for these promoter-less transcription reactions are shown in (FIGS. 1c and 3). The labeled RNA primer was HPLC purified runoff message from a separate T7 transcription reaction where $\gamma^{32}$P-GTP was the label. All transcription reactions were initiated by enzyme addition and terminated by adding equal volume of 8M urea. BME (0.7M final), tRNA (0.2 mg/ml final) and EDTA (0.4 mM final) were then added. The nucleotides were extracted after chloroform/isoamyl addition, and ethanol precipitated prior to denaturing gel electrophoresis.

To determine the fraction of the initiating molecules (labeled RNA primer) incorporated into full length transcripts, the bands corresponding to runoff RNA transcripts were excised from the gels and their radioactive counts determined and divided by the total counts of the transcription reaction. The fractional incorporation of γ-labeled GTP into aborted products 2–8 nucleotides (nts) long was likewise determined.

EXAMPLE 3

RNA Primer-Initiated Promoterless RNA Polymerase Transcription of a Single-Stranded DNA Template Using 7-mer and 8-mer RNA Primers The reactions and procedures were essentially similar to those of Example 2, above. The results are shown in FIG. 3 and are obtained from radiographs similar to FIG. 1c, which were provided by the procedures set forth in Example 2, above. The 7- or 8- nucleotide RNA primers were purified from separate runoff transcriptions and contain a $\gamma^{-32}$P label at their 5' guanine. The DNA concentrations in lanes 1 and 8 were 100 µM. The transcription reactions were allowed to proceed for 30 minutes. The mobilities of the expected 15 nt or 17 nt runoff RNAs were determined by loading reaction products of the type in FIG. 1a and 1b on the gel in FIG. 3, and the positions of the smaller products were determined by counting down successive n–1 RNAs in those lanes.

The molar concentrations of the runoff RNA transcripts were determined by multiplying the fraction of incorporated γ-labeled GTP or labeled primer incorporated into full length RNAs by the total concentration of these molecules (labeled plus unlabeled) at the start of the reaction. The results are reported in Table 2, below and illustrated by FIG. 3.

FIGS. 3a and 3b shows the comparison of the results obtained in Examples 1–3, above.

FIG. 3a (lanes 1–7) shows step-wise RNA transcription by T7 RNA polymerase of one of the strands on a double-stranded promoter/double-stranded template DNA molecules as compared to extension of a $\gamma^{32}$P-labeled RNA primer on a promoterless single-stranded template DNA molecule hybridized with said $\gamma^{32}$P-labeled eight-nucleotide RNA primer. The templates in the reaction of lanes 1–7 are the templates shown in Table 2, at (1a) and (1c), respectively. All the reactions contained T7 RNA polymerase and an 8-nucleotide (lanes 1–6) or 7-nucleotide (lane 7) primer that contained the only $\gamma^{32}$P-labeled species of the reaction. The 7-nucleotide primer lacked the 3'-terminal nucleotide of the 8-nucleotide primer shown in Table 2 at (1c) or (2c). The reaction loaded in lane 2 did not contain NTPs; lane 3 contained UTP; lane 4 contained UTP + GTP; lanes 1, 5, and 7 contained UTP + GTP + CTP; and lane 6 contained GTP + CTP + ATP. The locations of the initiating primers and those of the correct elongation products (based on the template sequences in Table 2 and the limited NTPs added) are shown to the left of the lanes. The RNA sizes formed in the presence of limed NTP substrates are predominantly those expected from the template sequences. However n–1 products (and to a lesser extent n+1 products) were also produced.

In Table 2, below, the large P represents the double stranded –17 to –1 sequence of class III T7 promoters, whose sequence is included as a segment in SEQ ID NOs: 1–4, 7–8, and 10–11. The fraction of initiating molecule ($\gamma$-$^{32}$P labeled GTP or 8 nt RNA) extended into the full length runoff RNA was determined after three hours of T7 transcription. The results are shown in FIG. 2. The bold sequences on the template strands indicate the eight-nucleotide primer binding sites. Dashed lines represent the absence of the non-template strand. Fully extended RNA yields after 3 hours were determined as described in the examples below.

TABLE 2

| Promoter/template | Substrates | Initiating molecule (total conc.) | Fraction extended | RNA Yield (µM) |
|---|---|---|---|---|
| 1a. +1            +15<br>   \|              \|<br>  P GGGACAATTGTGCCT<br>    CCCTGTTAACACGGA | GTP,ATP<br>CTP,UTP | pppG (1.5 mM) | 0.0063 | 9.5 |
| b.  P G-------------<br>     CCCTGTTAACACGGA | GTP,ATP<br>CTP,UTP | pppG (1.5 mM) | 0.0084 | 12.6 |
| c. 3'-TGACACCCTGTTAACACGGA-5' | UTP,GTP<br>CTP | 5'-pppGGGACAAU-3'<br>(0.12 mM) | 0.16 | 19.2 |
| 2a. +1            +17<br>   \|              \|<br>  P GGGACAATTTGGTGCTC<br>    CCCTGTTAAACCACGAG | GTP,ATP<br>CTP,UTP | pppG (1.5 mM) | 0.0023 | 3.5 |
| b.  P G----------------<br>     CCCTGTTAAACCACGAG | GTP,ATP<br>CTP,UTP | pppG (1.5 mM) | 0.0039 | 5.9 |
| c. 3'-TGACCCTGTTAAACCACGAG-5' | UTP,GTP<br>CTP | 5'-pppGGGACAAU-3'<br>(0.12 mM) | 0.056 | 6.7 |
| 3a. +1            +18<br>   \|              \|<br>  P GGGACAATGTCAGTGCAG<br>    CCCTGTTACAGTCACGTC | GTP,ATP<br>CTP,UTP | pppG (1.5 mM) | 0.0033 | 5.0 |
| b. 3'-GACTCCAG-<br>    CCCTGTTACAGTCACGTC-5' | GTP,ATP<br>CTP,UTP | 5'-pppGGGACAAU-3'<br>(0.12 mM) | 0.053 | 6.4 |

FIG. 3b (lanes 8–13) shows step-wise RNA transcription by T7 RNA polymerase of one of the strands on a double-stranded promoter/double-stranded template DNA molecules as compared to extension of a $\gamma^{32}$P-labeled RNA primer on a promoterless single-stranded template DNA molecule hybridized with said $\gamma^{32}$P-labeled eight-nucleotide RNA primer. The templates in the reaction of lanes 8 and 9–13 were the templates shown in Table 2, at (2a) and (2c), respectively. All the reactions contained T7 RNA polymerase and an 8-nucleotide (lanes 8–12) or 7-nucleotide (lane 13) primer that contained the only $\gamma^{32}$P-labeled species of the reaction. The 7-nucleotide primer lacked the 3'-terminal nucleotide of the 8-nucleotide primer shown in Table 2 at (1c) or (2c). The reaction loaded in lane 9 contained UTP; lane 10 contained UTP + GTP; lanes 8, 11 and 13 contained UTP + GTP + CTP; and lane 12 contained GTP + CTP + ATP. The locations of the initiating primers and the correct elongation products (based on the template sequences in the table and the limited NTPs added) are shown to the right of the lanes. The RNA sizes formed in the presence of limed NTP substrates are predominantly those Table 2, shows the promoter/template or template/primer sequences, substrates, initating molecules, fraction extended and RNA yield referred to or resulting from examples 1–3, below. FIGS. 1a, 1b, and 1c show the results from examples 1 and 2. FIGS. 2, 3a, and 3b compare the present promoterless RNA polymerase transcription to double-stranded promoter initiated RNA transcription.

The results from Examples 1–3, as presented in FIGS. 1–4, and in Table 2 show that the present invention method is advantageous as compared with conventional procedures.

The method according to the present invention allows synthesis of RNA molecules or DNA/RNA chimeras of any sequence. The use of chain terminators (3' dideoxynucleotide triphosphates (3' dNTPs)) in these reactions allows nucleic acid sequence determination according to the sequencing methods described, above, prior to the examples. Chains may be terminated by any other acceptable method. An example is the addition of a chelating agent such as ethylenedenedianoinetetraacetic acid (EDTA), which removes magnesium.

DNA/RNA chimeras are synthesized by extension of a DNA primer segment hybridized to the RNA template. Modified nucleotides may be selectively incorporated into an RNA chain by partial extension of a RNA primer hybridized to a DNA template, followed by subsequent extension(s), wherein one or more of the initial and subsequent extension steps provides a modified NTP as one of the starting materials.

The present invention provides an improved method for in vitro RNA synthesis, particularly mRNA. Improved RNA synthesis kits are provided with wider applications and improved RNA synthesis. The improvements in RNA synthesis include:

- reduction of abortive RNA chains and improved purity of RNA product;
- higher yield of RNA product (> 2 times the conventional yield)
- no requirement of promoter DNA or a specific polymerase binding co-factor
- the use of a single strand template coding segment instead of double strand
- the transcription elongation/initiation with any nucleotide
- transcription from any (pre-selected) point along a DNA or RNA template segment.

The present invention provides an improved method of DNA sequencing and/or an improved method of cDNA production. A RNA segment complimentary to the nucleotide sequence of any DNA target segment may be produced starting at any region of the target strand, by providing a RNA primer complementary to the starting point of that target region. The resulting RNA is reverse transcribed to yield cDNA, or is analyzed to determine the sequence of the DNA segment.

Progressively shorter or progressively longer RNA strands can be produced from selected target segments on the intact DNA segment to identify the DNA sequence. Adjacent target segments are progressively identified. The original DNA sequence does not need to be broken into smaller segments to target and transcribe a portion of the original DNA segment. This sequencing procedure is more accurate than prior art procedures since it eliminates guessing of how identified fragments fit together.

The RNA transcription process is stopped by the use of chain terminators when a desired chain length has been reached. The sequence of the segment is determined by separating the starting materials from the RNA produced and identifying the RNA sequence. Alternatively, the target segment sequence is determined by using the separated RNA to form a cDNA whose sequence is subsequently determined. An RNA primer is then produced which corresponds to the downstream end of the last sequenced target DNA segment. The target segment sequence determination process is repeated until the sequence for the entire intact DNA segment is obtained.

The present invention method for sequencing a DNA segment has several advantages over other DNA sequencing methods and kits. The most popular methods presently available for DNA sequencing are based on DNA polymerase mutant bound to thioredoxin (sold as Sequenase™). These methods rely on primer DNA extension on DNA strands. The method according to the present invention is simpler, is more cost effective, and is as powerful as the DNA primer method.

The present invention has the advantage of providing a means for quickly and accurately producing one or more cDNA segments from an intact DNA segment. These cDNA segments can be produced from a target area on a DNA segment without requiring fragmentation of the DNA segment. Thus, it is not necessary to isolate or obtain a short DNA segment limited to the target area to be transcribed.

An RNA primer is produced which corresponds to a desired initiation point of a target area on the intact DNA segment. The RNA primer is hybridized to the target area of the intact DNA segment and extended using the procedures according to the present invention. The RNA chain is terminated when the RNA segment is of proper length (any excess NTPs can be ligated before or after a cDNA molecule is formed). The strands are melted and the RNA segment is separated from the DNA segment.

A cDNA is formed from the RNA segment produced from the target area by using a reverse transcriptase and transcribing the RNA segment. The RNA segment hybridized to the cDNA portion of the double strand is digested away or separated after melting the strands.

The original template DNA segment (from which RNA was produced to subsequently produce cDNA) is conserved intact. If retrieved after transcription, melting, and separation of the RNA segment, it can be used again. Thus, the conserved intact DNA segment having more than one target area provides more than one cDNA without the template DNA segment being destroyed or broken. Moreover, the ability to produce a much smaller RNA segment from the larger intact DNA template allows for easier separation of the hybridized transcribed DNA template strand and RNA strands.

Also, the present invention provides a method of RNA sequencing using an RNA polymerase. As described above, an RNA primer or DNA primer can be elongated and resolved to determine the RNA sequence.

Kits are available for the enzymatic sequencing of long RNA sequences, but all suffer from disadvantages. All of the kits currently available for RNA sequencing rely on expensive and less processive enzymes (e.g., reverse transcriptase), or cannot extend both RNA and DNA primers. Thus, they require either a large amount of a particular starting material or a large amount of time to produce an adequate analytical sample. Frequently, a large amount of cDNA sample must be produced. The cDNA produced is then cloned into a vector to produce large amounts of RNA for analysis. Alternatively, the cDNA sample is multiplied by PCR procedures to provide an adequate DNA sample for sequencing. Such multiple steps allow more room for error as well as being expensive and time consuming.

Enzymes used for DNA sequencing by primer extension are listed in Table 3, below. Also, the last enzyme listed in Table 3 is T7 RNA polymerase as used according to the present invention. The properties and typical 1992 unit prices for the various enzymes are compared. The unit prices are from the Promega, 1992 catalog, USB, 1992 catalog, based on largest quantities sold. These enzymes are well-known in the art and readily available.

TABLE 3

Enzymes used for DNA sequencing by primer extension

| Enzyme | Primers | Processivity[f] (nts/falloff) | Rate of synthesis (nts/sec) | incorporation of chain terminators | 3'→5' exo activity | price/ un $ |
|---|---|---|---|---|---|---|
| Ideal |  | +++ | +++ | +++ | − |  |
| AMV RT | RNA or DNA | 22–30[f] | 4[a] | +++[a] | − | 0.8[p] |
| Klenow | DNA | 10[a] |  | +[a] | + | 0.3[p] |
| T7 DNA pol | DNA | 1–50[a,b] | 300[a] | ++ | +++[a] |  |
| Modified T7 DNA pol | DNA | 1–50[a,b] | 300[a] | ++ | − |  |
| Modified + Thioredoxin | DNA | 1000–10,000[a,b] | 300[a] | ++[a] | − | 0.4[u] |
| T7 RNA pol | RNA or DNA | 80,000[c] | 230[d] | +++[c] | − | 0.02[p,u] |

[a]Tabor et al., Proc. Ntal. Acad. Sci. U.S.A., 84, 4767–4771 (1987).
[b]Tabor et al., J. Biol. Chem. 262, 16212 (1987).
[c]Martin et al., Biochemistry 27, 2966–3974 (1988).
[d]Golomb et al., Proc. Natl. Acad. Sci. U.S.A., 71, 760–764 (1974).
[e]Axelrod et al., Biochemistry, 24, 5716–5723 (1985)(regarding 3'ddNTPs and chain termination).
[f]Kornberg, The Enzymes, 4th. ed, Academic Press, New York (1982)(defining processivity).
[p]Price from Promega, 1992 catalog, based on largest quantities sold.
[u]Price from USB, 1992 catalog, based on largest quantities sold.

As is clear from Table 3 there are many advantages to the method according to the present invention. The RNA polymerases according to the present are readily available, of low molecular weight, relatively inexpensive, will extend both RNA and DNA primers, have high processivity, have a high rate of synthesis, and efficiently incorporate chain a variety of chain terminators, which enhances nucleotide sequencing procedures. The high in vitro activity of these RNA polymerases may be attributed to their functional organization as a single-chain peptide.

New kits and methods based upon the present invention as described above allow faster sequencing of RNA segments with smaller starting samples. Such procedures and materials have wide uses in retroviral research and treatment. In those fields the starting genetic material is a RNA segment whose sequence needs to be identified as part of research and treatment.

The present invention has the advantage of permitting the synthesis of DNA/RNA chimeras. DNA primers are effeciently elongated with rNTP substrates to produce covalently linked DNA/RNA molecules on the same segment strand. Also, RNA segments produced by the present invention may be advantageously hybridized to complementary RNA primers, which are in turn elongated into RNA/DNA molecules using reverse transcriptase. Thus, the present invention provides adequate amounts of RNA template (by RNA primer extension on a DNA target segment). This supplements and enhances the known methods of using reverse transcriptase to produce chimeras. Accordingly, high chimera yields are obtained with the present invention. DNA/RNA chimera molecules have many potential pharmaceutical uses.

The present invention provides for the selective incorporation of base analogs along defined positions on an elongating RNA segment. Prior to the present invention, replacement of selected nucleotides with nucleoside triphosphate analogs was not possible.

A method according to the present invention uses a RNA polymerase and primer extension for selective elongation in the presence of these substrate analogs. A first round of chain elongation with substrate analogs leads to RNA products. Those RNA products are further extended in a second or third round of elongation with natural substrates. Table 1, above shows the many reported substrate analogs that the RNA polymerases used in the present invention can incorporate in an RNA elongating segment.

All references cited with respect to synthetic, preparative and analytical procedures represents the state of the art and to the extent necessary are incorporated herein by reference.

The present invention may be embodied in other specific forms without departing from the spirit or essential attributes thereof and, accordingly, reference should be made to the appended claims rather than to the examples in the foregoing specification, as indicating the scope of the invention. It is reasonably expected that an ordinary practitioner in this technical area, upon considering the present description and claims, can provide other equivalent forms of the present invention without departing from the spirit or essential attributes thereof. Accordingly, such variations and permutations are intended to be encompassed within the scope and claims of the present invention.

We claim:

1. A method for transcribing a DNA target segment, and thereby producing an RNA segment complementary to said DNA target segment, comprising:

(a) providing an DNA template segment containing the DNA target segment, (b) hybridizing to said DNA target segment a complementary RNA primer comprising 7 or more nucleotides to produce a modified template comprising a double-stranded hybrid DNA/RNA segment, and (c) exposing said modified template to an RNA polymerase selected from the group consisting of T7 RNA polymerase, T3 RNA polymerase and SP6 RNA polymerase which polymerase transcribes said DNA target segment by extension of said RNA primer, wherein the template segment lacks a promoter for said RNA polymerase.

2. A method according to claim 1, wherein said RNA polymerase is T7 RNA polymerase.

3. A method for transcribing an RNA target segment, and thereby producing a DNA/RNA chimera segment, wherein the RNA portion of said DNA/RNA chimera segment is complementary to said RNA target segment, comprising:

(a) providing an RNA template segment containing the RNA target segment, (b) hybridizing to said RNA target segment a complementary DNA primer comprising 7 or more nucleotides to produce a modified template comprising a double-stranded hybrid DNA/RNA segment, and (c) exposing said modified template to an RNA polymerase selected from the group consisting of T7 RNA polymerase, T3 RNA polymerase and SP6 RNA polymerase which polymerase transcribes said RNA target segment by extension of said DNA primer.

4. A method according to claim 3, wherein said RNA polymerase is T7 RNA polymerase.

5. A method for transcribing an RNA target segment according to claim 4 wherein the template segment lacks a promoter for said RNA polymerase.

6. A method of sequencing an RNA target segment comprising:

(a) providing a DNA primer segment comprising 7 or more nucleotides, wherein said DNA primer segment is complementary to a portion of said RNA target segment, (b) hybridizing said DNA primer segment to said RNA target segment to provide a modified RNA segment, and (c) exposing said modified RNA segment to an RNA polymerase selected from the group consisting of T7 RNA polymerase, T3 RNA polymerase and SP6 RNA polymerase which polymerase transcribes said modified RNA target segment by extension of said DNA primer to produce a DNA/RNA chimera segment hybridized to said modified RNA segment, wherein the target segment lacks a promoter for said RNA polymerase, (d) separating said DNA/RNA chimera segment from said RNA target segment strand by melting the double strands, and (e) determining the nucleotide sequence of said chimera segment obtained in step (d) to provide the nucleotide sequence of said RNA target segment.

7. (Amended) A method according to claim 6, wherein said RNA polymerase is T7 RNA polymerase.

8. A method of sequencing an RNA target segment comprising:

(a) providing a DNA primer segment comprising 7 or more nucleotides, wherein said DNA primer segment is complementary to a portion of said RNA target segment, (b) hybridizing said DNA primer segment to said RNA target segment to provide a modified RNA segment, (c) exposing said modified RNA segment to an RNA polymerase selected from the group consisting of T7 RNA polymerase, T3 RNA polymerase and SP6 RNA polymerase which polymerase transcribes said modified RNA target segment by extension of said DNA primer to produce a DNA/RNA chimera segment hybridized to said modified RNA segment, wherein the target segment lacks a promoter for said RNA polymerase, (d) separating said DNA/RNA chimera segment from said RNA target segment strand by melting the double strands, and (e) reverse transcribing said chimera segment obtained in step (d) to produce a cDNA segment hybridized to said chimera segment, (f) separating said cDNA segment from said DNA/RNA chimera segment, and (g) determining the nucleotide sequence of said cDNA segment to provide the nucleotide sequence of said RNA target segment.

9. A method according to claim 8, wherein said RNA polymerase is T7 RNA polymerase.

10. A method of sequencing a DNA target segment comprising:

(a) providing an RNA primer segment comprising 7 or more nucleotides, wherein said RNA primer segment is complementary to a portion of said DNA target segment, (b) hybridizing said RNA primer segment to said DNA target segment to provide a modified DNA segment, (c) exposing said modified DNA segment to an RNA polymerase selected from the group consisting of T7 RNA polymerase, T3 RNA polymerase and SP6 RNA polymerase which polymerase transcribes said DNA target segment by extension of said RNA primer to produce an RNA segment hybridized to said modified DNA segment, (d) separating said RNA segment from said DNA target segment, and (e) determining the nucleotide sequence of said RNA segment obtained in step (d) to provide the nucleotide sequence of said DNA target segment.

11. A method according to claim 10, wherein said RNA polymerase is T7 RNA polymerase.

12. A method of sequencing a DNA target segment according to claim 10 wherein the DNA target segment lacks a promoter for said RNA polymerase.

13. A method of sequencing a DNA target segment comprising:

(a) providing an RNA primer segment comprising 7 or more nucleotides, wherein said RNA primer segment is complementary to a portion of said DNA target segment, (b) hybridizing said RNA primer segment to said DNA target segment to provide a modified DNA segment, (c) exposing said modified DNA segment to an RNA polymerase selected from the group consisting of T7 RNA polymerase, T3 RNA polymerase and SP6 RNA polymerase which polymerase transcribes said modified DNA target segment by extension of said RNA primer to produce an RNA segment hybridized to said modified DNA segment, wherein the target segment lacks a promoter for said RNA polymerase.

(d) separating said RNA segment from said DNA target segment strand, and (e) reverse transcribing said RNA segment obtained in step (d) to produce a cDNA segment hybridized with said RNA segment, (f) separating said cDNA segment from said RNA segment, and (g) determining the nucleotide sequence of said cDNA segment to provide the nucleotide sequence of said DNA target segment.

14. A method according to claim 13, wherein said RNA polymerase is T7 RNA polymerase.

15. A method for producing an oligo- or polynucleotide segment comprising an RNA segment which incorporates one or more nucleoside triphosphate analogs by transcribing a DNA target segment to produce an RNA segment complementary to a portion of said DNA target segment, which method comprises:

(a) providing a DNA template segment containing the DNA target segment, (b) hybridizing to said DNA template segment a complementary RNA primer comprising 7 or more nucleotides to produce a modified template having a double-stranded hybrid DNA/RNA segment, and (c) exposing said modified template to an RNA polymerase selected from the group consisting of T7 RNA polymerase, T3 RNA polymerase and SP6 RNA polymerase which polymerase transcribes said DNA target segment by extension of said RNA primer to produce an RNA segment, wherein the template segment lacks a promoter for said RNA polymerase, and wherein during the transcription step one or more native nucleoside triphosphate reactants is/are replaced or supplemented by one or more nucleoside triphosphate analog reactants whereby the resulting RNA segment incorporates said nucleoside triphosphate analog.

16. A method according to claim 15, wherein said RNA polymerase is T7 RNA polymerase.

17. A method for producing an oligo- or polynucleotide segment comprising a DNA/RNA chimera segment having an RNA segment which incorporates one or more nucleoside triphosphate analogs by transcribing an RNA target segment and producing a DNA/RNA chimera segment wherein the RNA portion of said DNA/RNA chimera segment is complementary to said RNA target segment, comprising:

(a) providing an RNA template segment containing the RNA target segment, (b) hybridizing to said RNA template segment a complementary DNA primer comprising about 7 or more nucleotides to produce a modified template comprising a double-stranded hybrid DNA/RNA segment, and (c) exposing said modified template to an RNA polymerase selected from the group consisting of T7RNA polymerase, T3 RNA polymerse and SP6 RNA polymerase, which polymerase transcribes said RNA target segment by extension of said DNA primer to produce a DNA/RNA chimera segment, wherein during the transcription step one or more native nucleoside triphosphate reactants is/are replaced or supplemented by one or more nucleoside triphosphate analog reactants whereby the resulting DNA/RNA chimera segment incorporates said nucleoside triphosphate analog.

18. A method according to claim 17, wherein said RNA polymerase is T7 RNA polymerase.

19. A method for producing an oligo- or polynucleotide segment according to claim 17 wherein the template segment lacks a promoter for said RNA polymerase.

20. A method for producing an RNA/cDNA chimera segment, comprising;

(a) providing a DNA template segment containing a DNA target segment, (b) hybridizing to said DNA template segment a complementary RNA primer comprising 7 or more nucleotides to produce a modified template comprising a double-stranded hybrid DNA/RNA segment, and (c) exposing said modified template to an RNA polymerase selected from the group consisting of T7 RNA polymerase, T3 RNA polymerase and SP6 RNA polymerase which polymerase transcribes said DNA target segment by extension of said RNA primer to produce an RNA template, wherein the template segment lacks a promoter for said RNA polymerase, (d) separating said RNA template from said DNA target segment, (e) providing a second RNA primer which is complementary to a portion of said RNA template obtained in step (d), (f) hybridizing said second RNA primer with said RNA template to provide an RNA duplex of said RNA primer and RNA template, (g) exposing said RNA duplex to a reverse transcriptase, which transcribes said RNA segment by extending said RNA primer to produce an RNA/cDNA chimera segment hybridized with said RNA segment, and (h) separating said RNA/cDNA chimera from said RNA template.

21. A method according to claim 20, wherein said RNA polymerase is T7 RNA polymerase.

22. A method for transcribing a DNA target segment, and thereby producing a DNA/RNA chimera segment, wherein the DNA portion of said DNA/RNA chimera segment is complementary to said DNA target segment, comprising:

(a) providing a DNA template segment containing the DNA target segment, (b) hybridizing to said DNA target segment a complementary DNA primer comprising 7 or more nucleotides to produce a modified template, and (c) exposing said modified template to an RNA polymerase selected from the group consisting of T7 RNA polymerase, T3 RNA polymerase and SP6 RNA polymerase which polymerase transcribes said DNA target segment by extension of said DNA primer, wherein the template segment lacks a promoter for said RNA polymerase.

23. A method of sequencing a DNA target segment comprising:

(a) providing a DNA primer segment comprising 7 or more nucleotides, wherein said DNA primer segment is complementary to a portion of said DNA target segment, (b) hybridizing said DNA primer segment to said DNA target segment to provide a modified DNA segment, (c) exposing said modified DNA segment to an RNA polymerase selected from the group consisting of T7 RNA polymerase, T3 RNA polymerase and SP6 RNA polymerase which polymerase transcribes said modified DNA target segment by extension of said DNA primer to produce an RNA segment hybridized to said modified DNA segment, (d) separating said RNA segment from said DNA target segment strand, and (e) determining the nucleotide sequence of said RNA segment obtained in step (d) to provide the nucleotide sequence of said DNA target segment.

24. A method for producing an oligo- or polynucleotide segment comprising an DNA segment which incorporates one or more nucleoside triphosphate analogs by transcribing an RNA target segment to produce a DNA segment complementary to a portion of said RNA target segment, which method comprises:

(a) providing a RNA template segment containing the RNA target segment, (b) hybridizing to said RNA template segment a complementary RNA primer comprising 7 or more nucleotides to produce a modified template having a double-stranded hybrid DNA/RNA segment, and (c) exposing said modified template to an RNA polymerase selected from the group consisting of T7 RNA polymerase, T3 RNA polymerase and SP6 RNA polymerase which polymerase transcribes said DNA target segment by extension of said RNA primer to produce an RNA segment, and wherein during the transcription step one or more native nucleoside triphosphate reactants is/are replaced or supplemented by one or more nucleoside triphosphate analog reactants whereby the resulting DNA segment incorporates said nucleoside triphosphate analog.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
  ( A ) LENGTH: 29 Nucleotides
  ( B ) TYPE: nucleic acid
  ( C ) STRANDEDNESS: single stranded
  ( D ) TOPOLOGY: linear ( x i ) SEQUENCE DESCRIPTION: SEQ ID NO:1:

TAATACGACT TACTATGGGA ATTGTGCCT  29

( 2 ) INFORMATION FOR SEQ ID NO:2:

( i ) SEQUENCE CHARACTERISTICS:
    ( A ) LENGTH: 29 Nucleotides
    ( B ) TYPE: nucleic acid
    ( C ) STRANDEDNESS: single stranded
    ( D ) TOPOLOGY: linear ( x i ) SEQUENCE DESCRIPTION: SEQ ID NO:2:

CTTATGCTGA ATGATACCCT TAACACGGA  29

( 2 ) INFORMATION FOR SEQ ID NO:3:

( i ) SEQUENCE CHARACTERISTICS:
    ( A ) LENGTH: 18 Nucleotides
    ( B ) TYPE: nucleic acid
    ( C ) STRANDEDNESS: single stranded
    ( D ) TOPOLOGY: linear ( x i ) SEQUENCE DESCRIPTION: SEQ ID NO:3:

TAATACCGACT TACTATG  18

( 2 ) INFORMATION FOR SEQ ID NO:4:

( i ) SEQUENCE CHARACTERISTICS:
    ( A ) LENGTH: 20 Nucleotides
    ( B ) TYPE: nucleic acid
    ( C ) STRANDEDNESS: single stranded
    ( D ) TOPOLOGY: linear ( x i ) SEQUENCE DESCRIPTION: SEQ ID NO:4:

AGGCACAATT GTCCCACAGT  20

( 2 ) INFORMATION FOR SEQ ID NO:5:

( i ) SEQUENCE CHARACTERISTICS:
    ( A ) LENGTH: 8 Nucleotides
    ( B ) TYPE: nucleic acid
    ( C ) STRANDEDNESS: single stranded
    ( D ) TOPOLOGY: linear ( x i ) SEQUENCE DESCRIPTION: SEQ ID NO:5:

GGGACAAU  8

( 2 ) INFORMATION FOR SEQ ID NO:6:

( i ) SEQUENCE CHARACTERISTICS:
    ( A ) LENGTH: 8 Nucleotides
    ( B ) TYPE: nucleic acid
    ( C ) STRANDEDNESS: double stranded
    ( D ) TOPOLOGY: linear ( x i ) SEQUENCE DESCRIPTION: SEQ ID NO:6:

ATTGTCCC  8

( 2 ) INFORMATION FOR SEQ ID NO:7:

( i ) SEQUENCE CHARACTERISTICS:
    ( A ) LENGTH: 32 Nucleotides

```
        ( B ) TYPE: nucleic acid
        ( C ) STRANDEDNESS: single stranded
        ( D ) TOPOLOGY: linear ( x i ) SEQUENCE DESCRIPTION: SEQ ID NO:7:

TAATACGACT  TACTATGGGA  CAATTTGGTC  TC          32

( 2 ) INFORMATION FOR SEQ ID NO:8:

( i ) SEQUENCE CHARACTERISTICS:
        ( A ) LENGTH: 32 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:8:

CTTATGCTGA  ATGATACCCT  GTTAAACCAG  AG          32

( 2 ) INFORMATION FOR SEQ ID NO:9:

( i ) SEQUENCE CHARACTERISTICS:
        ( A ) LENGTH: 20 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:9:

GAGCACCAAA  TTGTCCCAGT              20

( 2 ) INFORMATION FOR SEQ ID NO:10:

( i ) SEQUENCE CHARACTERISTICS:
        ( A ) LENGTH: 18 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:10:

GGGACAATGT  CAGTGCAG                18

( 2 ) INFORMATION FOR SEQ ID NO:11:

( i ) SEQUENCE CHARACTERISTICS:
        ( A ) LENGTH: 18 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:11:

CCCTGTTACA  GTCACGTC                18

( 2 ) INFORMATION FOR SEQ ID NO:12:

( i ) SEQUENCE CHARACTERISTICS:
        ( A ) LENGTH: 18 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:12:

CTGCACTGAC  ATTGTCCC                18
```